US009192165B2

(12) United States Patent
Rose et al.

(10) Patent No.: US 9,192,165 B2
(45) Date of Patent: Nov. 24, 2015

(54) METHOD AND DEVICE FOR ATTRACTING BLOOD-SUCKING ARTHROPODS

(75) Inventors: Andreas Rose, Regensburg (DE); Angela Koeckritz, Berlin (DE); Michael Kant, Berlin (DE); Reinhard Eckelt, Rostock (DE); Dang-Lanh Hoang, Berlin (DE); Johannes Kant, legal representative, Erkner (DE)

(73) Assignee: Biogents Ag, Regensburg (DE)

( * ) Notice: Subject to any disclaimer, the term of this patent is extended or adjusted under 35 U.S.C. 154(b) by 0 days.

(21) Appl. No.: 14/001,286

(22) PCT Filed: Feb. 24, 2012

(86) PCT No.: PCT/EP2012/053169
§ 371 (c)(1),
(2), (4) Date: Jul. 18, 2014

(87) PCT Pub. No.: WO2012/113910
PCT Pub. Date: Aug. 30, 2012

(65) Prior Publication Data
US 2014/0322360 A1    Oct. 30, 2014

(30) Foreign Application Priority Data
Feb. 25, 2011   (DE) .......................... 10 2011 012 472

(51) Int. Cl.
*A01N 59/04*    (2006.01)
*A01M 1/02*    (2006.01)
*C01B 31/20*    (2006.01)
*A01M 1/06*    (2006.01)

(52) U.S. Cl.
CPC ............... *A01N 59/04* (2013.01); *A01M 1/023* (2013.01); *A01M 1/06* (2013.01); *C01B 31/20* (2013.01)

(58) Field of Classification Search
CPC ........ A01M 1/023; A01M 1/06; A01N 59/04; A01N 59/00; A01N 31/00; A01N 31/02; C01B 31/20
See application file for complete search history.

(56) References Cited

U.S. PATENT DOCUMENTS

| 5,145,825 A * | 9/1992 | Deeba et al. ............... 502/242 |
| 2009/0209790 A1 * | 8/2009 | Coventry ................... 568/955 |

FOREIGN PATENT DOCUMENTS

| DE | 69918405 T2 | 6/2005 |
| WO | 99/37145 | 7/1999 |
| WO | 2004/071189 | 8/2004 |
| WO | 2005/092020 | 10/2005 |
| WO | 2006/108244 | 10/2006 |

OTHER PUBLICATIONS

Hebben et al., Applied Catalysis A: General 388: 225-231 (2010).*

* cited by examiner

*Primary Examiner* — Sue Liu
*Assistant Examiner* — Thor Nielsen
(74) *Attorney, Agent, or Firm* — Simmons Perrine Moyer Bergman PLC (57) ABSTRACT

The invention relates to a method for producing CO2 for attracting bloodsucking arthropods (2). In this method, at least one liquid or solid organic substance (11) is reacted in an oxidation process in a targeted manner, one portion completely and another partially, thus forming, in addition to CO2, H2O and heat, at least one further partial oxidation product (P). The invention further relates to a device (1*a*, 1*b*) for generating CO2, said device (1*a*, 1*b*) comprising a storage means (10) for at least one liquid or solid organic substance (11) and an evaporation module (14) for the liquid or solid organic substance (11). The device (1*a*, 1*b*) comprises a reactor module (16) for the controlled oxidation and partial oxidation of the at least one liquid or solid organic substance (11); a control unit (80); and means (13, 18, 21, 22, 26) for regulating the oxidation and partial oxidation process. The means (13, 18, 21, 22, 26) for regulating the oxidation and partial oxidation process can be regulated via the control unit (80), hence allowing defined reaction conditions to be set in the reactor module (16) for the targeted control of the oxidation and partial oxidation process.

18 Claims, 6 Drawing Sheets

METHOD AND DEVICE FOR ATTRACTING BLOOD-SUCKING ARTHROPODS

CLAIM OF PRIORITY

The present application is a national application of PCT/EP2012/053169, filed on Feb. 24, 2012, which in turn claims the benefit of Germany Application No. DE10 2011 012 472.1, filed on Feb. 25, 2011, both of which are incorporated by reference.

FIELD OF THE INVENTION

The present invention relates to a method and a device for attracting blood-sucking arthropods.

PRIOR ART

Blood-sucking arthropods, especially insects and arachnids, are a danger to the health of people residing in the tropics and subtropics, but also of people residing in temperate latitudes, because they can transmit disease. Against many of these diseases there are neither vaccines nor specific therapies. Therefore the prevention of these diseases by addressing the carriers is of particular importance.

So far non-specific insecticides are used in pest control. For certain species, the breeding sites can be searched and destroyed. For personal protection repellents and insecticide vaporizers are used. Especially bed nets are used to protect against bites of nocturnal blood-sucking arthropods. Also catching devices, which attract and trap or kill blood-sucking insects, are used for pest control.

To increase the effectiveness of these traps, physical and chemical attractants are used. Furthermore, it is conceivable that the arthropods are attracted onto surfaces or into structures with a suitable attractant. Thereby the arthropods are retained on adhesive surfaces or the surfaces are provided with contact toxins or with pathogens to the target organisms that infect and thus destroy the target organisms, their species-specific sex partners or their offspring.

The target organisms can be at least partly lured away from their hosts and/or captured with suitable and strong attractants. Thereby an at least temporary protection is achieved.

For example, WO 9811774 A1 describes an insect trap that uses carbon dioxide and/or other gaseous attractants, to attract and catch insects in a bag. The carbon dioxide is hereby supplied to the trap directly in a gaseous form.

The document WO 2004/071 189 A1 describes a mosquito trap, wherein the $CO_2$ is generated by combustion of propane, gasoline or kerosene. The combustion of propane to produce $CO_2$ as an attractant is disadvantageous in several respects. The combustion takes place by means of an open flame at high temperatures (more than 1000° C.). Depending on the quality and purity of the used propane gas, the combustion produces pollutants. The $CO_2$ produced by the combustion is therefore purified with a catalytic converter located downstream. This catalytic converter may contaminate or age during use, so that the attractive effect of the trap can decrease dramatically over time. Then the trap or at least the catalytic converter must be replaced.

The object of the invention is to provide a method and a device for attracting insects, wherein an attractant composition containing $CO_2$ is produced in an easy, secure and efficient manner. The method and the device should not have the above-mentioned disadvantages of known insect traps.

The above object is achieved by a method and a device described below.

DESCRIPTION

The invention relates to a method for attracting blood-sucking arthropods, especially insects and arachnids. The arthropods are particularly attracted to $CO_2$. The arthropods can be caught and retained and/or killed in a catching device, especially an insect trap. For the generation of the $CO_2$ at least one liquid or solid organic substance is reacted in an oxidation process. In particular, the term organic substances is used to describe an organic substance or a mixture of organic compounds.

According to the invention the substance is reacted in an oxidation process in a targeted manner, wherein one portion of the substance is oxidized completely and another portion is oxidized partially. In addition to $CO_2$, $H_2O$ and heat at least one other partial oxidation product is generated. This partial oxidation product causes an amplification of the particular luring effect of the attractant mixture. Also, the heat generated during the oxidation process represents another positive factor for the attraction of the insects or the like. According to one embodiment described below, the heat can also be diverted and used elsewhere.

The oxidation process of the organic substance is in particular a catalytic oxidation process.

According to a preferred embodiment, the at least one liquid or solid organic substance is evaporated before the oxidation process, in particular before the catalytic oxidation process, and mixed with air to form a reaction gas mixture. The amount of additionally supplied air can hereby be adjusted or regulated; in particular the oxygen content is adjusted to be insufficient to fully oxidize the whole fuel substance to $CO_2$. Instead, the amount of additionally supplied air can be adjusted in such a way that particularly attractive oxidation product/partial oxidation product mixtures are formed. A targeted control of the combustion process is possible by a selective adjustment of the mixing ratio of fuel substance and oxygen.

Alternatively, the regulation of the combustion process can be carried out via an adjustment of the reaction temperature. For example, it may be advantageous that the fuel substance is preheated in order to obtain desired proportions of oxidation products and partial oxidation product(s) in the combustion product. Similarly, a targeted cooling can be used advantageously. The reaction temperature can also be influenced via constructive measures, for example, using different levels of insulation in different parts of the device. Other possibilities for the specific regulation of the combustion process known to the expert in the relevant technical field are also encompassed by the invention.

If the oxidation or partial oxidation is done via catalytic combustion, then a noble metal catalyst is preferably used as a catalyst. The noble metal of the catalyst is selected from a group consisting of Pd, Pt, Ru, Ag, Au, Rh or a mixture of at least two of these metals. The carrier material is an inorganic material, preferably an oxide or a spinel structure, especially $Al_2O_3$, $SiO_2$, $Al_2O_3$—$SiO_2$, $TiO_2$, $ZrO_2$, a rare earth oxide, $Fe_2O_3$, a zeolithe, a molecular sieve or a hydrocalcite.

Furthermore, other suitable catalysts, in particular semi-noble metal catalysts with Cu or transition metal supported catalysts with Mn or the like, mixed metal catalysts or catalysts with other, preferably corrosion-resistant metals like Ti can be used.

The combustion of the at least one liquid or solid organic substance can be selectively adjusted, for example by means of a control unit, so that certain partial oxidation products are produced in a defined ratio to $CO_2$. For example, the reaction conditions—that is the reaction temperature and/or the amount of available oxygen, etc.—will be specially selected for the conversion of ethanol, so that defined amounts of ethanal (also known as acetaldehyde), acetic acid, ethyl acetate and/or diethyl ether are produced and released together with the $CO_2$, for example amounts between 0.1 ppm and 10% each, preferentially between 0.1 ppm and 5% each. For this purpose, a control unit may be provided. The control unit may, for example, comprise a chemical sensor, for analyzing the composition of the oxidation products and partial oxidation products. The control unit may further comprise means for regulating the air supply or the reaction temperature or the like. The desired composition of combustion products can be input, for example, into the control unit. Because of the chemical data obtained by sensors, the control unit regulates the supply of air and/or the reaction temperature etc. correspondingly, thereby adjusting the amount of oxidation products and partial oxidation products.

A particular advantage of the catalytic process is that combustion can be carried out without an open flame. Thus, the method can be carried out at temperatures well below the combustion temperature of the liquid or solid organic substance used. This reduces the fire hazard and increases the safety for the user.

The heat formed during the reaction can be used according to another embodiment in order to generate electric voltage and drive the associated catching device at least partially. For example, at least one Seebeck element (also known as thermoelectric devices or Peltier devices) can be used to ensure the operation of the electrical components of the device for performing the described method and/or its associated catching device at least partially.

The liquid or solid organic substance used to produce the $CO_2$ is chosen from a group consisting of alcohols, ketones, aldehydes, hydrocarbons, olefins, ethers, carboxylic acid esters, fats and oils. Preferentially alcohols, especially methanol, ethanol or methylated spirits are used.

Thus carbon dioxide is produced as a product of the total oxidation with the described method. In parallel, a portion of partially oxidized product/partially oxidized products is generated specifically, which also act as (an) attractant(s) for blood-sucking insects and increase the attractiveness of the carbon dioxide.

The invention further relates to a device for producing $CO_2$ for attracting blood-sucking arthropods. This device is suitable, for example, for use in combination with a catching device for insects, blood-sucking arthropods, etc. The device comprises a storage means and a vaporization module for the vaporization of the at least one liquid or solid organic reactant. According to the invention, the device comprises a reactor module for the controlled oxidation and partial oxidation of the at least one liquid or solid organic substance. Further, the reactor module may comprise means for regulating the oxidation process and the partial oxidation process and a control unit for regulating the oxidation process and/or partial oxidation process. Particularly defined reaction conditions can be set in the reactor module, so that the amount of resulting partial oxidation product(s) can be adjusted in a targeted manner. For example, the device can comprise a controllable air supply or the like for the targeted regulation of the oxygen supply. Thereby the amount and/or composition of the at least one generated partial oxidation product can be adjusted specifically. The resulting partial oxidation products, e.g. aldehydes, ketones, carboxylic acids, esters, ethers etc., are admixed with the resulting stream of $CO_2$ at low levels, thereby increasing the attractive effect of the device. Additionally or alternatively, heating and/or cooling elements may be provided, which serve to adjust the reaction temperature, pre-tempering the reactant etc.

The device may further comprise a catalyst in its reactor module for the controlled catalytic oxidation and controlled catalytic partial oxidation of the at least one liquid or solid organic substance.

The advantages of the method and device relative to the conventionally known methods and devices for producing carbon dioxide, in particular in conjunction with catching devices consist mainly in a substantial simplification of the technical operation of the oxidation process. Through the use of an organic reactant in a liquid or solid state instead of, for example, propane, the safety of the device can be increased significantly for the user. A simpler and less dangerous decentralized use of the device is possible. The organic substance can be used easily without requiring the use of compressed gas cylinders, making the storage of the fuel easier. This can be seen as a particular advantage for use in rural areas having a poor infrastructure. Another advantage of the device and method is that low amounts of organic reactant are required to achieve comparable attraction results. Therefore it is possible to produce the entire device smaller and lighter, making it easier to carry for the user.

In the catalytic conversion of the fuel material $CO_2$ and at least one partial oxidation product is preferably produced by a catalytic oxidation and/or partial oxidation. Preferably there is no open flame combustion. In particular, the formation of carbon black or similar constituents can be avoided, which would damage the catalytic converter or can deter the mosquitoes or the like. Since the device does not require an open flame, it is possible to make the device smaller, whereby it can also be produced less expensively.

With the device according to the invention and with the method according to the invention $CO_2$-containing attractant mixtures can thus be produced easily, quickly and economically. Especially mixtures can be produced that show a higher attraction for blood-sucking arthropods than pure $CO_2$. In particular, mosquitoes etc. show a greater orientation to an attractant mixture containing $CO_2$.

It is thus easily possible to produce attractant mixtures that are particularly attractive to certain types of blood-sucking arthropods. This allows a targeted attraction of certain species. This can be used advantageously, for example, for research purposes.

DESCRIPTION OF THE DRAWINGS

The following examples are intended to illustrate the invention and its advantages with reference to the accompanying figures. The size ratios of the individual elements in the figures do not necessarily reflect the real size ratios. It is to be understood that in some instances various aspects of the invention may be shown exaggerated or enlarged to facilitate an understanding of the invention.

The same or equivalent elements of the invention are designated by identical reference characters. Furthermore and for the sake of clarity, only the reference characters relevant for describing the respective figure are provided. It should be understood that the embodiments described are only examples and they are not intended to limit the scope of the disclosure.

Figure 1:
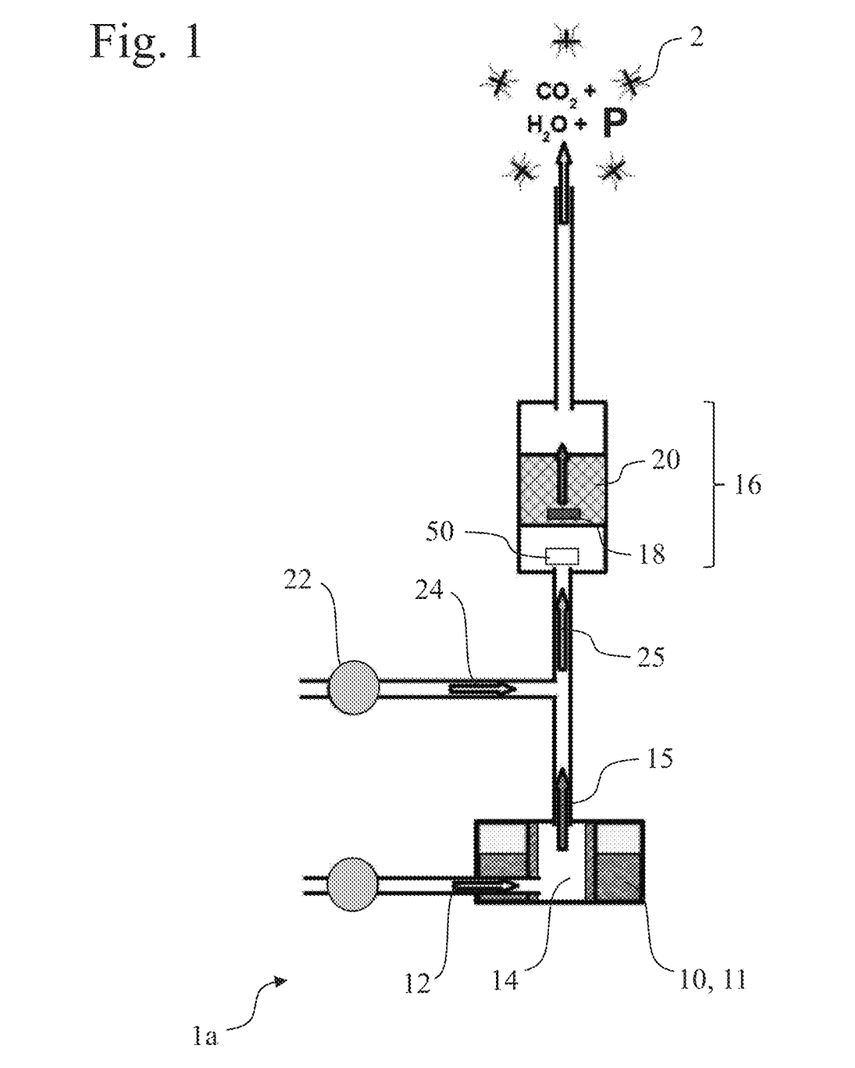
FIG. 1 shows a first embodiment of a device for generating $CO_2$ for attracting blood-sucking arthropods.

FIG. 1 shows a first embodiment of a device 1a for generating an attractant mixture containing $CO_2$ for attracting blood-sucking arthropods 2. The attractant mixture is especially produced by catalytic oxidation and partial oxidation. The device 1a comprises a storage unit 10 for the liquid or solid organic substance 11 to be oxidized. First, a variable or fixed air stream 12 is produced. The air stream 12 is mixed with substance 11 in a suitable vaporization module 14 and the first gas mixture 15 generated thereby is then fed to a reactor module 16.

The reactor module 16 comprises a catalyst bed 20 and a heating element 18 for setting the required starting temperature for the catalytic full oxidation reaction and partial oxidation reaction of the substance 11. The reactor module 16 further includes a flame arrestor 50. This serves as a protection device, in case the first gas mixture 15 should inadvertently ignite in the reactor chamber 16, for example due to overheating of the catalyst. Due to a malfunction a flame might be produced from the first fuel-air gas mixture 15. The flame arrestor 50 prevents the flame from entering the vaporization module 14.

Furthermore, the device 1a may include a control device 22, in particular a controllable and/or firmly adjustable air supply etc. Thereby the reaction conditions can be adjusted in a targeted manner, so that controlled amounts of $CO_2$ and controlled amounts of the desired partial oxidation products P can be generated. Preferably, the additionally supplied air 24 is added to the first gas mixture 15 obtained from vaporized substance 11 and air 12 before the reactor module 16, thereby adjusting the optimum ratio of organic substance 11 and oxygen for the catalytic conversion.

The second gas mixture 25, consisting of vaporized substance 11 and air 12 or additionally supplied air 24, flows through the flame arrestor 50 and then it flows through the catalyst bed 20. In the catalyst bed 20 the catalytic oxidation reaction is started by heating with a suitable heat source, in particular with a heating element 18 or after an autocatalytic ignition. In particular, the volumetric flow rate through the catalyst bed is between approximately 50 ml/min and 800 ml/min. The volumetric flow rate depends primarily on the amount of $CO_2$ that is to be produced. Other components that affect the volumetric flow rate and that can be set accordingly are the type of fuel used and the amount of additionally supplied air.

In the oxidation reaction $CO_2$, $H_2O$ and heat and possibly partial oxidation products P are generated. These are released by the device 1a and cause the attraction of arthropods 2. The partial oxidation products P increase the attractive effect of the device 1a. The attractive effect is increased up to 50% or more compared to conventional devices emitting $CO_2$. In particular, there is an increase in the attractive effect of the mixture containing oxidation products and the partial oxidation products of up to 60% compared to a complete combustion of a fuel. With the device according to the invention, for example, a tripling of the catching rate could be achieved.

Figure 2:
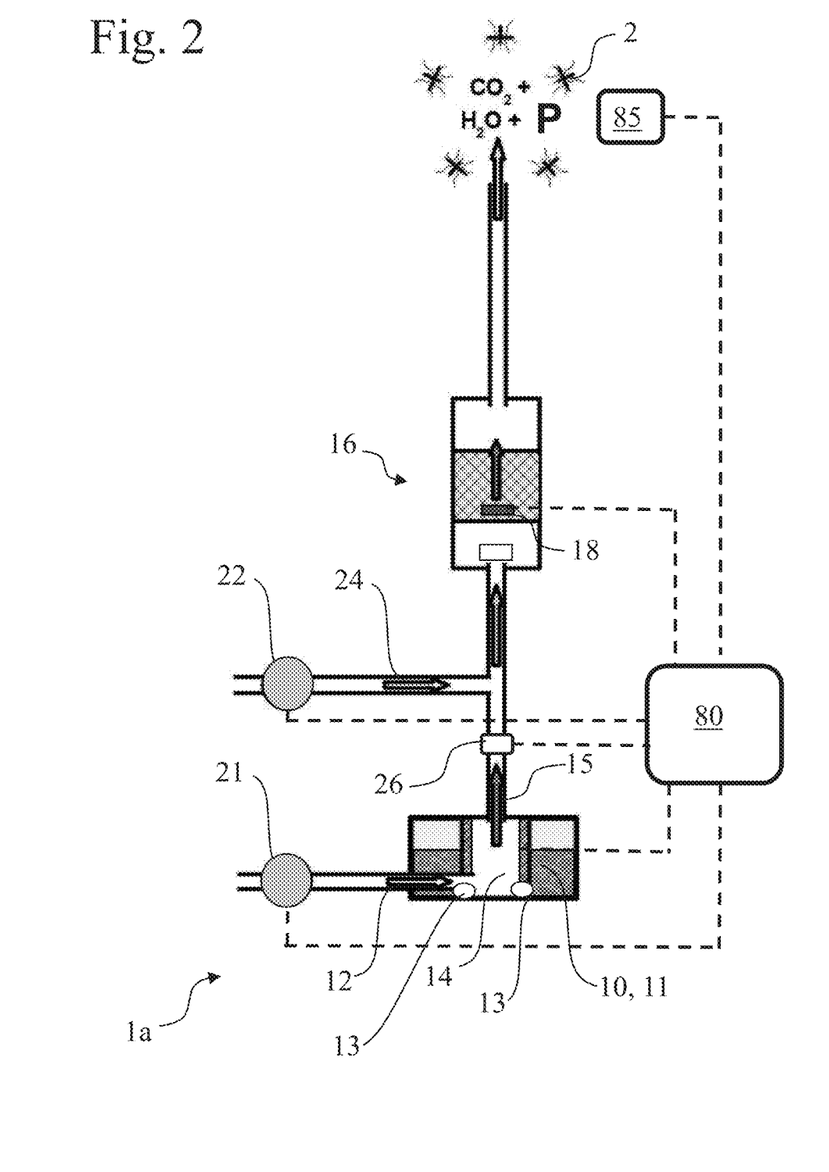
FIG. 2 shows a first embodiment of a device according to the invention according to FIG. 1 with a controller.

FIG. 2 shows a first embodiment of a device 1a according to FIG. 1 with a controller 80. For example, the controller regulates the air supply 22 of additionally supplied air 24 added to the first gas mixture 15. Furthermore, it can be provided that the controller 80 regulates the heating element 18 and hence the reaction temperature in the reactor module 16. Thereby the amount of partial oxidation can also be adjusted. FIG. 2 also shows an optional controllable air supply 21, via which the amount of air 12, which is fed into the vaporization module 14, may be selectively adjusted by the controller 80. Moreover, adjustable or controllable means 13 can be provided in the vaporization module 14, which control the release of fuel substance 11 into the vaporization module 14. Behind the vaporization module 14 and prior to admixing the additionally supplied air 24, a valve 26 can be arranged that adjusts the quantity of first gas mixture 15, which is passed on to the reactor module 16 per unit time.

Further, a chemical sensor 85 is shown. The sensor determines the composition of the oxidation products and partial oxidation products ($CO_2$ and P). The sensor 85 is connected to the controller 80 with one of the described means 21, 22 for regulating the air supply or with a means 13, 26 for adjusting the first gas mixture 15 or with a means 18 for setting the reaction temperature or the like. The desired composition of combustion products—i.e. $CO_2$, $H_2O$ and partial oxidation product(s) P—can be entered, for example, into the controller 80. Because of the chemical data obtained by sensors, the controller 80 regulates the supply of air 21, 22 and/or the reaction temperature 18 etc. correspondingly, to adjust the composition of the attractant mixture accordingly.

Figure 3:
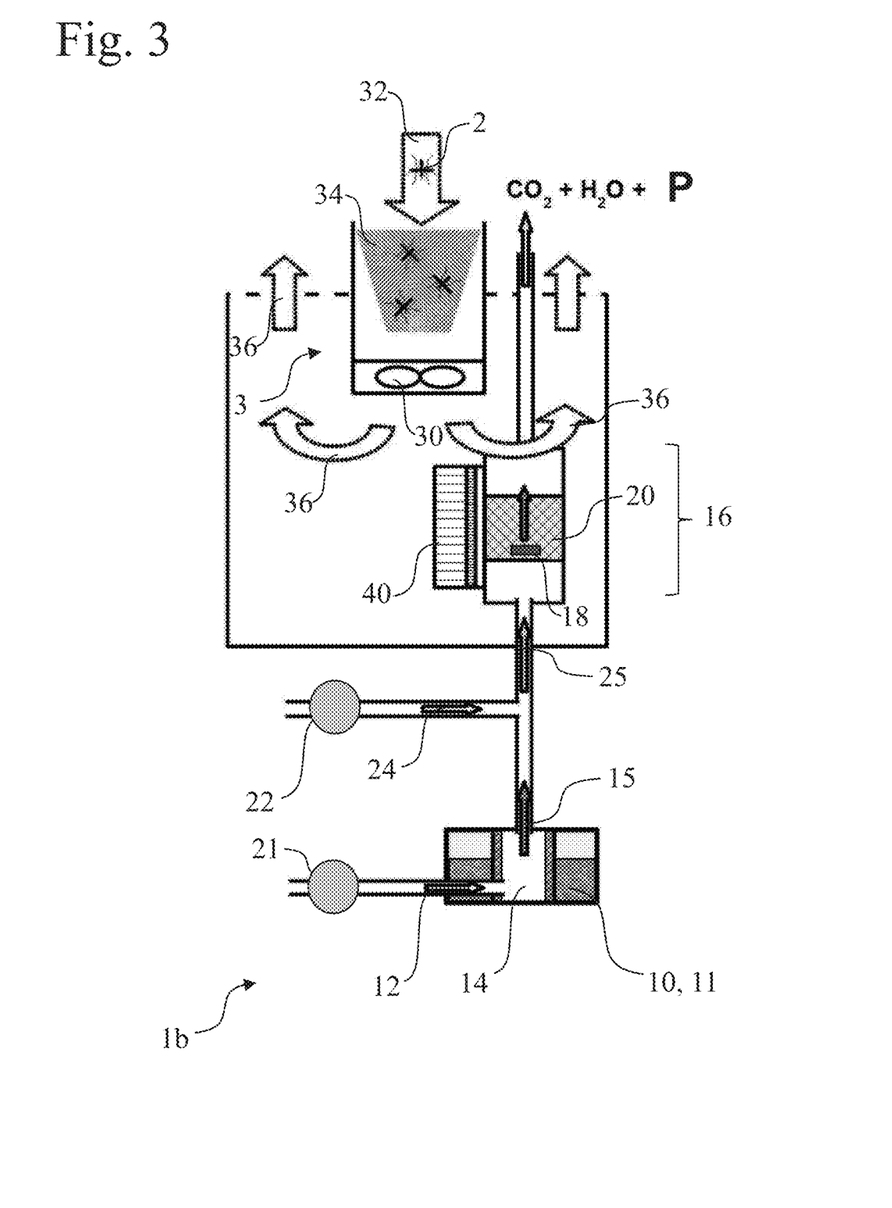
FIG. 3 shows a second embodiment of a device for generating $CO_2$ for attracting and trapping blood-sucking arthropods.

FIG. 3 shows a second embodiment of a device 1b for generating an attractant mixture containing $CO_2$ for attracting blood-sucking arthropods 2. This is coupled directly to a device 3 for catching or temporarily retaining the attracted arthropods 2.

The $CO_2$-producing device 1b is arranged adjacent to the catching device 3. Thereby the oxidation products $CO_2$, $H_2O$ and at least one partial oxidation product P are released in the vicinity of an intake device 30. The attracted arthropods 2 are sucked into the intake device 30 by an inflow current 32 and are retained in a suitable collecting device 34. Further non-exclusive possibilities known to the expert in the art are, for example, attracting arthropods 2 onto bonding surfaces or attracting arthropods 2 onto surfaces or into labyrinths that are provided with contact toxins or organisms that are pathogenic to arthropods 2 or their descendants.

The reactor module 16 may be arranged in such a position that it heats, for example, the effluent air stream 36 emitted from the catching device 3 and/or that it outputs radiant heat, which is additionally attractive to the blood-sucking arthropods 2.

The heat produced by the reactor module 16 may, for example, be used to generate an electric voltage through the use of one or more Seebeck elements 40. This electric voltage can ensure at least partly the operation of the electrical components of the device 1b and/or its associated catching device 3.

Figure 4:
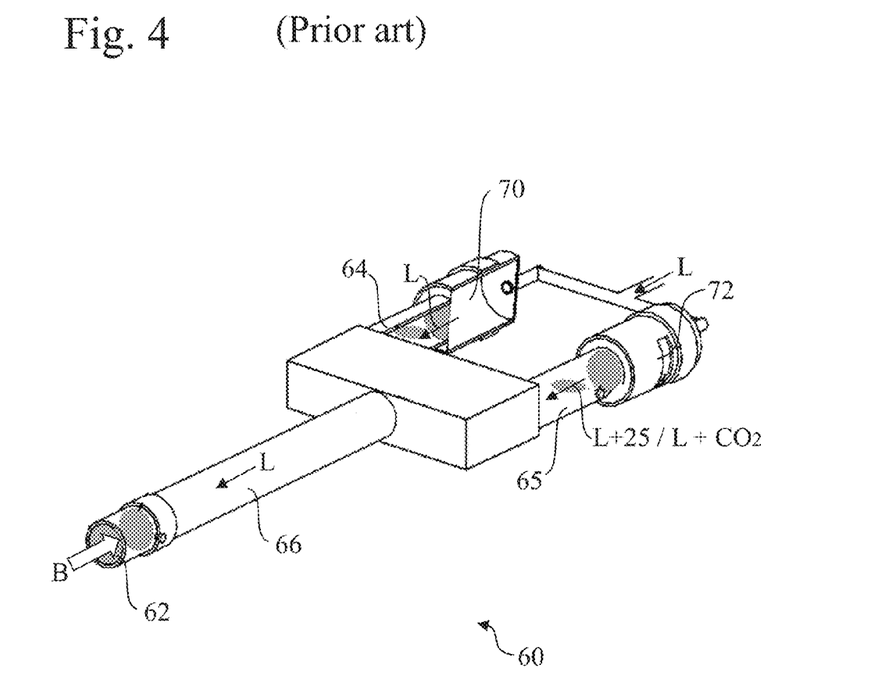
FIG. 4 shows an olfactometer to measure the attractiveness of an attractant/attractant mixture (prior art).

FIG. 4 shows an olfactometer 60 for measuring the attractiveness of an attractant or an attractant mixture according to the known prior art. Olfactometer tests are particularly useful during product development. They are used to filter out the most promising candidate substances from a number of interesting attractants or repellents quickly and cost-effectively. In particular, the olfactometer 60 has the form of a "Y". A cage with piercing joyful female mosquitoes is connected to the lower end 62 of the "Y" of the air conditioned tubular system of the olfactometer 60. The two arms 64 and 65 of the "Y" each include the control chamber 70 and test chamber 72. Air L flows through both chambers 70, 72 and is then combined in the base leg 66 of the "Y". During the phase when the stimulus is given, the test mosquitoes can fly into the direction of movement B into the olfactometer 60 and choose between the test chamber 72 with air containing the stimulus and the control chamber 70 containing clean air. Air L flows through the olfactometer 60 in the direction opposite to the direction of movement B of the mosquitoes, the air L being entrained with the attractant from the test chamber 72.

Firstly, the activation or mobilization of the test mosquitoes is determined. This refers to a non-directional fly away of the mosquitoes when a stimulus is given. In particular, this corresponds to the percentage of mosquitoes that fly into the olfactometer 60 at all. Then the orientation is further determined by counting the number of mosquitoes in the test chamber 72. This determines the percentage of mosquitoes that specifically fly towards the test stimulus.

An olfactometer 60 may, for example, be used to test potentially repellent substances. These are for example applied on a filter paper and held into the apparatus together with a human finger. As a comparison, the human finger is tested alone. The reduction of the attractiveness of the finger during the test with the repellent test substance gives information about the repellent potential of the tested substance. Attractive scent stimuli are e.g. introduced into the apparatus in the form of dispensers or by means of compressed air with certain flow rates. They are also compared with tests of a human finger, in order to obtain indications of the potential attraction for mosquitoes.

In this case, pure $CO_2$ is introduced in the test chamber 72 in a series of control experiments. In parallel, oxidation products/partial oxidation products $CO_2$ and P from the device 1 according to the invention are introduced into the test chamber 72 of a further olfactometer 60 (see FIGS. 1 to 3) and the results of the two experiments are compared.

Figure 5:
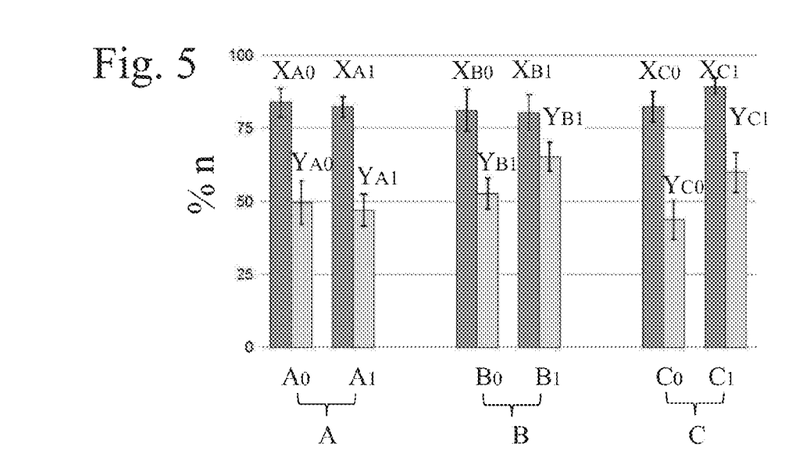
FIG. 5 to FIG. 7 compare the attractiveness of pure $CO_2$ with the attractiveness of the attractant mixture produced with a device according to the invention.
Figure 6:
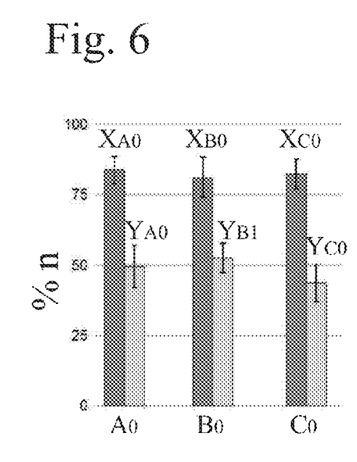
Figure 7:
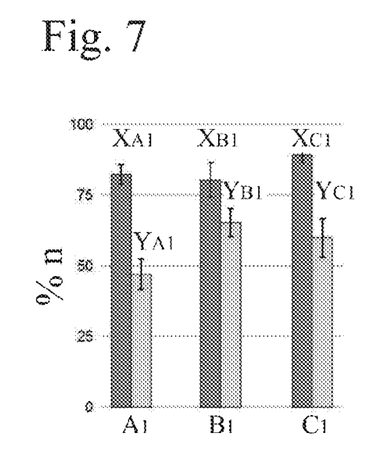

FIGS. 5 to 7 compare the attractiveness of pure $CO_2$ with the attractiveness of the attractant mixture of a device according to the invention. In these experiments, the attractiveness of different concentrations $A_0$, $B_0$, $C_0$ of pure $CO_2$ were compared with the attractiveness of different attractant mixtures $A_1$, $B_1$, $C_1$ in an olfactometer 60 (see FIG. 4). The respective test conditions are listed in the table:

| test series A | $A_0$ | 25 ml $CO_2$ | |
| --- | --- | --- | --- |
| | $A_1$ | 100 ml ethanol-saturated air + 100 ml additionally supplied air | =25 ml $CO_2$ → complete oxidation |
| test series B | $B_0$ | 50 ml $CO_2$ | |
| | $B_1$ | 200 ml ethanol-saturated air + 100 ml additionally supplied air | <50 ml $CO_2$ → contains partial oxidation products |
| test series C | $C_0$ | 75 ml $CO_2$ | |
| | $C_1$ | 300 ml ethanol-saturated air + 200 ml additionally supplied air | <75 ml $CO_2$ → contains partial oxidation products |

In particular, different amounts of ethanol-saturated air and additionally supplied air were used in the test series $A_1$, $B_1$, $C_1$ and combusted in a device 1 according to the invention. Depending on how much additional air is used, specifically a complete oxidation (test trial $A_1$) or a partial oxidation (test trials $B_1$, $C_1$) can be adjusted.

Comparing the control test series $A_0$, $B_0$, $C_0$ with each other (see also FIG. 6), in which pure $CO_2$ is used as attractant, an undirected activation $X_{A0}$, $X_{B0}$ and $X_{C0}$ of about 83% ($X_{A0}$: 84%; $X_{B0}$: 81.5%; and $X_{C0}$: 82.4%) of the number n of mosquito females used and a directional orientation $Y_{A0}$, $Y_{B0}$ and $Y_{C0}$ of about 50% ($Y_{A0}$: 50%; $Y_{B0}$: 52.1%; and $Y_{C0}$: 43.7%) can be found, regardless of the $CO_2$ concentration used. This means that the presence of $CO_2$ is a clear attractant, wherein the concentration of the $CO_2$ has no noticeable influence.

Comparing the results in test series A, then the following picture results: The combustion of 100 ml ethanol-saturated air with 100 ml additionally supplied air (experiment $A_1$) is a complete oxidation which results in 25 ml $CO_2$. When this result is compared with the control test series $A_0$, wherein 25 ml $CO_2$-gas are used directly, it results in a similar activation $X_{A0}$ and $X_{A1}$ of about 84% and 82.4% of the number n of mosquitoes used. Furthermore, there is a similar orientation $Y_{A0}$ and $Y_{A1}$ of about 50% and 47.1% of the number n of mosquitoes used. With complete oxidation of the fuel ethanol, the attractiveness of the attractant mixture generated with the device according to the invention corresponds to the attractiveness of traps directly using $CO_2$.

Comparing the results in test series B, then the following picture results: The combustion of 200 ml ethanol saturated air with 100 ml additionally supplied air (experiment $B_1$) produces less than 50 ml $CO_2$, since the oxygen content is insufficient for complete oxidation and thus partial oxidation products are also produced. When this result is compared with the control test series $B_0$, wherein 50 ml $CO_2$-gas are used directly, it results in a similar activation $X_{B0}$ and $X_{B1}$ of about 81.5% of the number n of mosquitoes used. However, the orientation $Y_{B1}$ of the attractant mixture produced by the oxidation/partial oxidation according to the invention is significantly increased. In particular the orientation $Y_{B1}$ is about 65%, while the orientation $Y_{B0}$ in the control group is approximately 50%. This represents an increase of attractiveness with respect to the orientation Y of approximately 30%.

Comparing the results in test series C, then the following picture results: The combustion of 300 ml ethanol saturated air with 200 ml additionally supplied air (experiment $C_1$) less than 75 ml $CO_2$ are produced, since the oxygen content is insufficient for complete oxidation and thus partial oxidation products are also produced. When this result is compared with the control test series $C_0$, wherein 75 ml $CO_2$-gas are used directly, it results in an improved activation $X_{C1}$ of about 88% compared to the activation $X_{C0}$ of about 81.5% of the control group. This represents an increase of attractiveness X by approximately 9%. Furthermore, the orientation $Y_{C1}$ is increased significantly. In particular the orientation $Y_{C1}$ is at about 60%, meanwhile the orientation $Y_{C0}$ of the control group is about 43%. This represents an increase of attractiveness with respect to the orientation Y by approximately 40%.

Further comparing the results of trial series $A_1$, $B_1$, $C_1$ with each other (see FIG. 7), whereby different attractant mixtures each are produced from ethanol-saturated air and additionally supplied air by means of a device according to the invention, it shows that the activation and/or the orientation of the mosquitoes can be improved by a targeted adjustment of the amount of partial oxidation and by regulating the additional air supply. Both factors are indicators for a better attractive effect of the combustion product.

Figure 8:
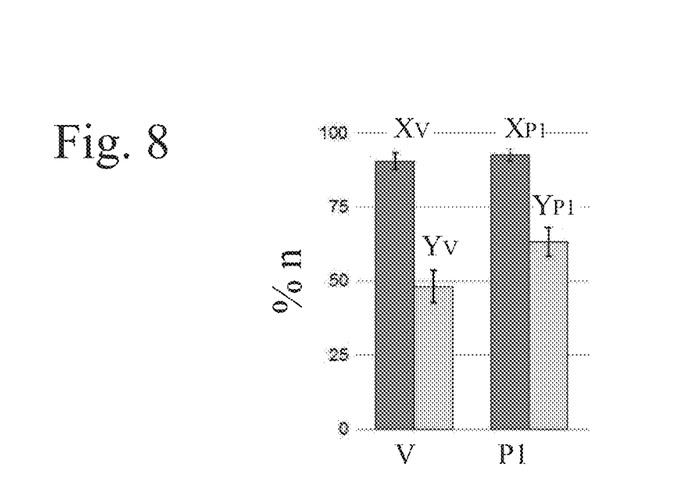
FIGS. 8 and 9 compare the attractiveness of the attractant mixture, produced with a device according to the invention at different admixture of air.
Figure 9:
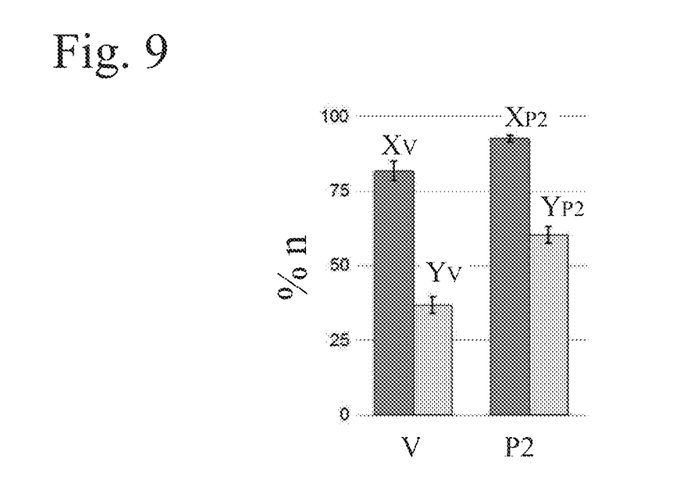

FIGS. 8 and 9 compare the attractiveness of an attractant mixture at different admixture of air.

| | | |
|---|---|---|
| V | 100 ml ethanol-saturated air + 100 ml additionally supplied air | =25 ml $CO_2$ → complete oxidation |
| $P_1$ | 100 ml ethanol-saturated air + 75 ml additionally supplied air | <25 ml $CO_2$ → contains partial oxidation products |
| $P_2$ | 100 ml ethanol-saturated air + 50 ml additionally supplied air | <25 ml $CO_2$ → contains partial oxidation products |

FIG. 8 shows experiments done in parallel with a control group V with complete oxidation of ethanol to 25 ml $CO_2$ in the device according to the invention and with a test group $P_1$ with oxidation and partial oxidation of ethanol in the device according to the invention. These experiments confirm the results of the test series C of FIG. 5 and show an enhanced activation $X_{P1}$ of approximately 93% compared to $X_V$ of about 89% in the control group V. This represents an increase of attractiveness in relation to the activation X of by about 5%. Furthermore, an improved orientation $Y_{P1}$ of the mosquitoes of about 65% compared to an orientation $Y_V$ of approximately 48% can be found. This represents an increase of attractiveness with respect to the orientation Y of approximately 35%.

FIG. 9 shows parallel experiments of a control group V with complete oxidation of ethanol to 25 ml $CO_2$ and a test group $P_2$ with oxidation and partial oxidation of ethanol in the device according to the invention. The amounts of additionally supplied air were further reduced compared with the test results shown in FIG. 8, so that even more partial oxidation products are produced. Hereby also an improved activation $X_{P1}$ of approximately 93% compared to approximately 81% of $X_V$ is obtained. This represents an increase of attractiveness X with respect to the activation by approximately 15%. Furthermore, an improved orientation $Y_{P2}$ of approximately 60% of the mosquitoes compared to approximately 37% of $Y_V$ can be found. This represents an increase of attractiveness with respect to the orientation Y by approximately 62%.

The results shown in FIGS. 8 and 9 illustrate once more that a targeted control of oxidation and partial oxidation can be used to improve the attractiveness, especially it can be used to improve the orientation Y.

The invention has been described with reference to preferred embodiments. To the expert it is also conceivable, however, to make changes and modifications without leaving the scope of protection of the appended claims.

LIST OF REFERENCE NUMBERS

| | |
|---|---|
| 1a/1b | device for generating $CO_2$ |
| 2 | blood-sucking arthropods |
| 3 | catching device |
| 10 | storage unit |
| 11 | organic substance |
| 12 | air stream |
| 13 | controllable means |
| 14 | vaporization module |
| 15 | first gas mixture |
| 16 | reactor module |
| 17 | heating element |
| 20 | catalyst bed |
| 21 | first control device |
| 22 | second control device |
| 24 | additionally supplied air |
| 25 | second gas mixture |
| 26 | valve |
| 30 | intake device |
| 32 | inflow current |
| 34 | collecting device |
| 36 | effluent air stream |
| 40 | Seebeck element |
| 50 | flame arrestor |
| 60 | olfactometer |
| 62 | lower end |
| 64 | arm |
| 65 | arm |
| 66 | base leg |
| 70 | control chamber |
| 72 | test chamber |
| 80 | controller |
| 85 | sensor |
| B | direction of movement |
| L | air |
| n | number |
| P | partial oxidation product |
| X | activation |
| Y | orientation |

The invention claimed is:

1. A method for generating $CO_2$ for attracting blood-sucking arthropods, comprising: reacting at least one liquid or solid organic substance in an oxidation process, wherein the oxidation process is partly a full oxidation and partly a partial oxidation, resulting in an attractant mixture comprising at least one partial oxidation product (P) in addition to $CO_2$ and $H_2O$, wherein the organic substance is selected from a group consisting of alcohols, ketones, aldehydes, hydrocarbons, olefins, ethers, carboxylic acid esters, fats or oils,
   wherein the oxidation and the partial oxidation are regulated through means for regulating the oxidation process and the partial oxidation process and a control unit, wherein at least one partial oxidation product (P) is formed in a ratio to $CO_2$, wherein between 0.1 ppm and 10% of the partial oxidation product (P) is generated.

2. The method of claim 1, wherein the oxidation process is a catalytic oxidation process.

3. The method of claim 2, wherein the oxidation and the partial oxidation is regulated through means for regulating the oxidation process and partial oxidation process and a control unit, wherein the at least one partial oxidization product (P) is selected from ethanal, acetic acid, ethyl acetate and/or diethyl ether.

4. The method of claim 3, wherein:
   a desired composition of $CO_2$ and the partial oxidation product (P) is input into the control unit;
   a chemical analysis of the composition of $CO_2$ and the partial oxidation product (P) or partial oxidation products is carried out; and
   means for the regulation are adjusted by the control unit.

5. The method of claim 1, wherein the reaction conditions for the oxidation process are adjusted by specifically regulating and/or adjusting the reaction temperature and/or the available oxygen and/or the amount of available fuel substance.

6. The method of claim 5, wherein the at least one liquid or solid organic substance is vaporized prior to the catalytic oxidation process and partial oxidation process and mixed with air in a defined ratio and wherein the catalytic oxidation process and partial oxidation process are catalyzed by a noble metal catalyst, a semi-noble metal catalyst, a transition metal supported catalyst, a mixed metal catalyst or a catalyst support with at least one other.

7. The method of claim 6, wherein the method is carried out at a temperature, which is less than the combustion temperature of the liquid or solid organic substance used during combustion with an open flame and wherein the at least one liquid or solid organic substance is selected from a group consisting of alcohols, ketones, aldehydes, hydrocarbons, olefins, ethers, carboxylic acid esters, fats and/or oils.

8. The method of claim 7, wherein the blood-sucking arthropods are caught in a catching device and retained and/or killed.

9. A device (1a, 1b) according to FIGS. 1 to 3 for generating $CO_2$, whereby the device (1a, 1b) comprises:
- a storage means (10) for at least one liquid or solid organic substance (11);
- a vaporization module (14) for the liquid or solid organic substance (11);
- a reactor module (16) for the controlled oxidation and partial oxidation of the at least one liquid or solid organic substance (11);
- a control unit (80);
- a chemical sensor (85);
- means (13, 18, 21, 22, 26) for the regulation of the oxidation process and the partial oxidation process, wherein the means (13, 18, 21, 22, 26) for regulating the oxidation process and the partial oxidation process are adjustable by the control unit (80) using the data obtained by the chemical sensor (85) and wherein the means for regulating the oxidation process and the partial oxidation process are means (18) for setting the reaction temperature and/or means (21, 22) for regulating the air supply,
- wherein defined reaction conditions can be set in the reactor module (16) for the targeted control of the oxidation process and the partial oxidation process, and
- wherein the organic substance (11) is selected from a group consisting of alcohols, ketones, aldehydes, hydrocarbons, olefins, ethers, carboxylic acid esters, fats or oils.

10. The device (1a, 1b) of claim 9, wherein the means for regulating the oxidation process and the partial oxidation process are means (18) for setting the reaction temperature and/or means (21, 22) for regulating the air supply.

11. The device (1a, 1b) of claim 10, wherein the reactor module (16) comprises a catalyst (20) for the targeted control of the catalyzed oxidation process and partial oxidation process of the at least one liquid or solid organic substance (11), wherein the catalyst (20) is a noble metal catalyst, a semi-noble metal catalyst, a transition metal supported catalyst, a mixed metal catalyst or a catalyst with at least one other, preferably corrosion-resistant metal and wherein the metal of the catalyst (20) is selected from the group consisting of Pd, Pt, Ru, Ag, Au, Rh, Cu, Mn or a mixture of at least two of these metals and wherein the support material is an inorganic support.

12. The device (1a, 1b) of claim 11, wherein the reactor module (16) comprises a heating element (18) and/or a flame arrestor (50).

13. The device (1a, 1b) of claim 9, further comprising a catching device (3) for attracting and catching blood-sucking arthropods (2) and/or further comprising a Seebeck element (40) for generating an electrical voltage, wherein the device (1a, 1b) and/or the catching device (3) are at least partially driven with the electric voltage.

14. The method of claim 1 wherein the oxidation and the partial oxidation are regulated through a valve, a heating element, a controllable air supply, a control device, a valve, or combinations thereof.

15. The device of claim 9 wherein the means for regulation the oxidation process and the partial oxidation process comprises a valve (13), a heating element (18), a controllable air supply (21), a control device (22), a valve (26), or combinations thereof.

16. The method of claim 6, wherein the catalytic oxidation process and partial oxidation process are catalyzed by a corrosion-resistant metal.

17. The method of claim 7, wherein the alcohols are selected from methanol or ethanol.

18. The method of claim 11, wherein the support material has an oxide structure or a spinel structure.

* * * * *